Figure 1:
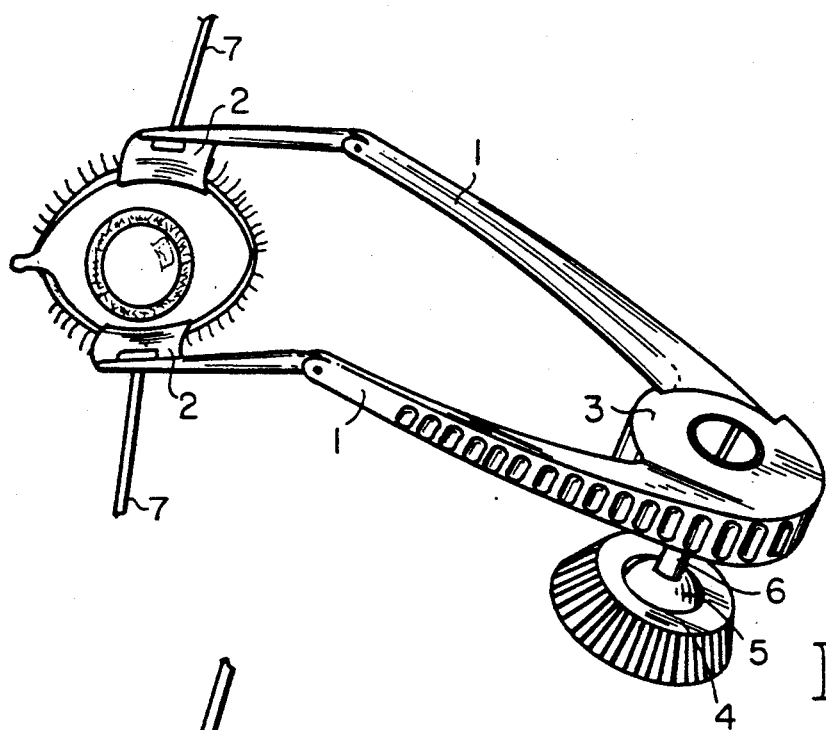

United States Patent [19]

Grounauer

[11] Patent Number: 5,070,860
[45] Date of Patent: Dec. 10, 1991

[54] RETRACTOR DEVICE FOR HUMAN OR ANIMAL TISSUE

[76] Inventor: Pierre-Alain Grounauer, Rue de l'Ale 38, CH - 1003 Lausanne, Switzerland

[21] Appl. No.: 397,446
[22] PCT Filed: Nov. 17, 1988
[86] PCT No.: PCT/CH88/00217
    § 371 Date: Jul. 21, 1989
    § 102(e) Date: Jul. 21, 1989
[87] PCT Pub. No.: WO89/05131
    PCT Pub. Date: Jun. 15, 1989

[30] Foreign Application Priority Data

Dec. 4, 1987 [CH] Switzerland ............ 4735/87

[51] Int. Cl.$^5$ ............................................. A61B 17/02
[52] U.S. Cl. .......................................... 128/20; 128/17
[58] Field of Search ............................ 128/17, 18, 20

[56] References Cited

U.S. PATENT DOCUMENTS

| 1,706,500 | 3/1929 | Smith | 128/20 |
|---|---|---|---|
| 2,702,540 | 2/1955 | Debeh | 128/20 |
| 3,490,455 | 1/1970 | Illig | 128/20 |
| 3,651,689 | 3/1972 | Haddad | 128/17 |
| 4,037,589 | 7/1977 | McReynolds | 128/20 |
| 4,321,916 | 3/1982 | McKee | 128/20 |
| 4,412,532 | 11/1983 | Anthony | 128/20 |
| 4,621,619 | 11/1986 | Sharpe | 128/20 |

FOREIGN PATENT DOCUMENTS

| 2951664A1 | 2/1981 | Denmark . |
|---|---|---|
| 3535045A1 | 4/1987 | Denmark . |
| 0156218 | 10/1985 | European Pat. Off. . |

OTHER PUBLICATIONS

Eisner, Georg, Eye Surgery, An Introduction to Operative Technique (1980), pp. 73-80.

*Primary Examiner*—Edward M. Coven
*Assistant Examiner*—Mark S. Graham
*Attorney, Agent, or Firm*—Woodward, Emhardt, Naughton, Moriarty & McNett

[57] ABSTRACT

A retractor of human or animal tissue comprises two arms with a spoon at one end, the other end being connected to a housing. The housing contains a spring which produces a force which spreads the two arms apart. The foot is connected to the housing by means of the spindle and a ball-joint. The lower face of the foot has a double-face adhesive.

5 Claims, 2 Drawing Sheets

RETRACTOR DEVICE FOR HUMAN OR ANIMAL TISSUE

The mechanical devices for the retraction of human or animal tissues have to make it possible to see the subjacent anatomic elements, thereby making visible an operative area. These devices for making accessible previously concealed tissues are particularly useful in connection with microsurgical operations, particularly of the eye or for the functional exploration of the latter. They enable the edges of a cutaneous incision to be kept spaced apart, without any force other than that provided by the said device.

Known at the present time are numerous devices which have for their purpose to retract the eyelids and to hold them spaced from the eyeball. In particular, one example of such a device is described in U.S. Pat. No. 4,037,589. This device is very rudimentary and comprises only a metallic loop, the concave ends of which permit the retraction of the eyelids. Another example of known device is described in U.S. Pat. No. 1,706,500; this device is also rudimentary in that the spoon badly fit to the eyelid, furthermore the coplanar arrangement of the arms does not permit the desired raising for a surgical operation. All these devices are inscribed in the strategy of the operative safety, the analysis of which is the condition for the actual success of the surgery. This analysis comprises an exhaustive study of all the instruments which are to be used by the surgeon, particularly for the retraction of the eyelids, which is a preliminary step in connection with any eye operation. All the basic elements of this surgery are described in the book entitled EYE SURGERY, Georg Eisner Springer Verlag, 1980. Pages 73 to 78 in particular give information concerning the particular mechanical properties which have to be possessed by the devices which are related to the said description. It is particularly mentioned therein that the eyeball should no longer be in contact with the rims of the eyelids, nor the retractor proper. It has now been found that the existing devices do in fact have numerous disadvantages.

Figure 2:
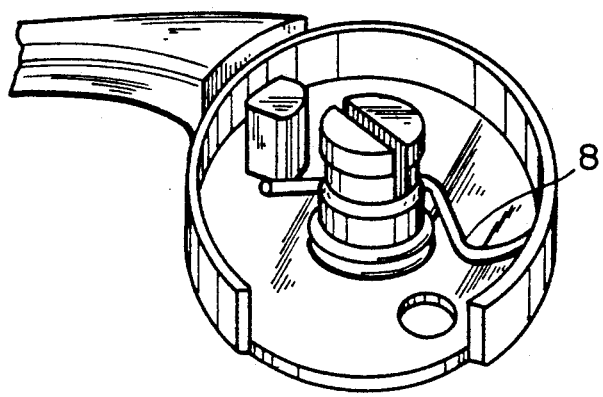
Figure 3:
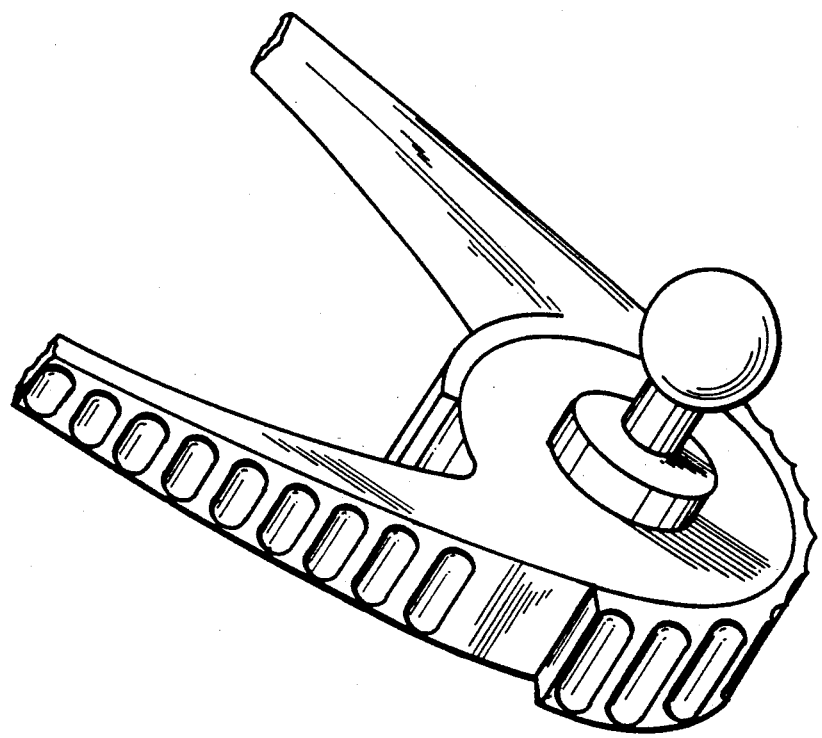

Therefore it is also the object of the present invention, such as claimed herein, to obviate these disadvantages by providing a retractor device for human or animal tissue, comprising two arms, which are each terminated at one of the ends by a spoon, the other end being connected to a casing, characterized in that the spoons have two curvatures adapted to the palpebral circle and to the curvature of the eyeball. One embodiment of the retractor device according to the invention is now to be described, by way of example, by reference to the accompanying drawings, wherein:

FIG. 1 is a view of the retractor device, seen in elevation and showing its application during an eye operation, FIG. 2 is a detail view of the spoons and the casing, FIG. 3 is a detail view of the casing and its arbor.

The general arrangement, such as that shown in FIG. 1, is characterized in that the separate parts by which the desired object is achieved are : the spoons 2, the strips 7, the arms 1, the casing 3, the spindle 6, the ball-and-socket joint 5, the foot 4. All these elements are connected to one another in such manner that, once stuck on the temple, the device, by means of its arms, holds the lower and upper eyelids spaced and raised, from the time when their free edge is engaged in the concavity of the spoons 2. On the other hand, these latter are movable and articulated with the ends of the arms, in order to permit the desired raising, an action still maintained by the strips 7 bearing on the external face of the spoon 2 and held on the operative field by an adhesive. This mechanism assures the supplementary raising which could possibly be needed by the surgeon. The self-supporting character of this arrangement enables it to be used in the operating room and also in connection with certain functional explorations of the eye. In particular, this device permits the spacing apart and the raising of the eyelids, even on a seated patient.

The device as described comprises, at the end of each arm 1, a casing 3 in which is disposed a spring 8. This latter, brought under tension, tends automatically to retract the eyelids or the edges of any other operating field, without the cooperation of a second surgeon being necessary. The operative field is in this way freed from any element which reduces the freedom of the surgical movements and liable to make more difficult any access to the tissues.

Once the device as described is placed in position, it assures the raising of the eyelids relatively to the eyeball, as a consequence of the articulation which exists between the spoons 2 and the arms 1. What is thereby established is a palpebral circle, so-called as a safety circle, spacing the eyelids from the eyeball, so as to avoid these eyelids causing an excess of intraocular pressure. This is particularly useful in the case where there is local anasthesia of the eye, this process being increasingly used in the case of ambulatory operations, particularly of cataracts. The possibility of being able to use strips which extend to the interior of the spoons increases still more the spacing of the eyelids. The use of adhesive strips or of clips permits the effect obtained to be maintained, while still assuring the immobility of the device, the foot of which is stuck by double face self-adhesive on the temporal side of the orbit, this assuring the immobility thereof.

Summarising, this device has three characteristics; it is self-supporting, self-retracting, self-elevating.

The spoons 2 are adapted to the shape of the eyeball and the eyelids, i.e. they have the curvatures required in the frontal and horizontal anatomic plane. Of variable dimensions, they are adapted to all the eyeball sizes, from the newly born to the adult. Contrary to other devices, they have a solid surface, in order to trap the eyelashes which would be able to come into contact with the instruments or the suture wires and cause infections. On the other hand, the pressure on the eyelids is more uniformly distributed, thus avoiding certain complications described with other devices, namely the post-operation paralyses of the upper eyelid. They have a gap in which fine strips are able to be slid, this contributing to the immobility of the said device. They are hinged with the arms, in order to permit a regulation of the function of raising.

The strips 7 make possible a regulation and maintenance of the desired raising, while at the same time forming fixation points for the operative field, thus permitting the stability of the assembly.

The arms 1 permit the transmission to the spoons 2 of the force liberated by the spring 8 under tension included in the casing 3. The arms 1 and the spoons 2 are hinged in a same plane.

The spring 8 makes possible to assure the auto-retraction function. By way of example, the scientific article described in OPHTALMIC SURGERY, Vol. 14, pages 575-578, 1983, gives values which permit of determining the force of the spring 8.

The spindle 6 and the ball-and-socket joint 5 permit of transmitting all the positions required in order to be adapted to the particular anatomic conditions of each patient.

The casing 3 may be separated from the spindle 6, in order to permit the surgeon to expose another part of the eyeball.

The lower face of the foot 4 is covered with a double face adhesive, permitting the adhesion on the external orbital wall, corresponding to the temple of the patient. The contact surface has been chosen so as to assure a maximum degree of immobility.

This device may be manufactured from all materials which have biocompatible properties.

Summarising, this retractor device offers the following advantages, as compared with the known devices:

1. Immobility. This is assured by three fixed points integral with the operative field and maintaining the palpebral circle spaced from the eyeball.
2. Adaptability. The device is adaptable to the anatomic angles by a first adjustment of the axis of the leg held in a foot and then by a fine adjustment, due to the pivoting of the spoons.
3. This device is profiled and designed in such manner that there is no risk of any screw or rod retaining and holding captive the surgical wires when they are placed in position.
4. The retraction of the eyelids is effected by solid surface spoons, having a slit situated on their front face, through which are passed two safety strips.
5. The symmetry of the device itself permits it to be positioned equally either on the right eye or the left eye.
6. The device is so conceived that it can be injection moulded from medical plastic material, of which the advantage is, inter alia, its ligthness. Moreover, it may be produced by moulding and injection in series, this reducing the cost of the device and permitting the single use thereof.
7. It is non-magnetisable.
8. It is radio-transparent.

I claim:

1. A retractor device for human or animal tissues, and more particularly for retracting upper and lower eyelids to expose the underlying eyeball for surgery, comprising:

a pair of retracting arms each having corresponding first and second ends;

a pair of corresponding spoons, each having a first curvature adapted to the shape of an eyeball and a second curvature adapted to the shape of an eyelid, articulatingly mounted to the first ends of said retracting arms;

casing means disposed at the second ends of said retracting arms joining said second ends in a cooperating relationship and biasing the first ends of said retracting arms into retracted positions; and a strip attached to each one of said corresponding spoons, each strip having means to removably affix the strip to human or animal tissue in a position that biases said spoons away from the eyeball as said first ends of said retracting arms are being biased into retracted positions.

2. A retractor device for retracting the upper and lower eyelids of a human or an animal to expose the underlying eyeball for surgery, comprising:

a pair of retracting arms each having corresponding first and second ends;

a pair of corresponding spoons, each having a first curvature adapted to the shape of an eyeball and a second curvature adapted to the shape of an eyelid, pivotally mounted to the first ends of said retracting arms to move in substantially planar relationship therewith;

casing means disposed at the corresponding second ends of said retracting arms, joining said corresponding second ends in a cooperating relationship and biasing the first ends of said retracting arms into retracted positions; and a strip attached to each of said corresponding spoons, each strip having means to removably affix the strip to human or animal tissue in a position that biases said spoons away from the eyeball as said first ends of said retracting arms are biased into retracted positions.

3. The retractor device of claim 2 wherein said casing means includes a spring arranged to bias the first ends of said retracting arms into retracted positions.

4. The retractor device of claim 2 wherein said casing means includes an articulating foot.

5. The retractor device of claim 4 wherein said articulating foot includes means to removably affix said foot to human or animal tissue.

* * * * *

UNITED STATES PATENT AND TRADEMARK OFFICE
CERTIFICATE OF CORRECTION

PATENT NO. :  5,070,860

DATED :  December 10, 1991

INVENTOR(S) :  Pierre-Alain Grounauer

It is certified that error appears in the above-identified patent and that said Letters Patent is hereby corrected as shown below:

In the name of the "Attorney, Agent of Firm" on the title page of the patent, change "Woodward" to --Woodard--.

In column 1, line 11, after the word "latter" insert a period.

In column 1, line 34, after the word "Eisner" insert a comma.

Figure 1A:
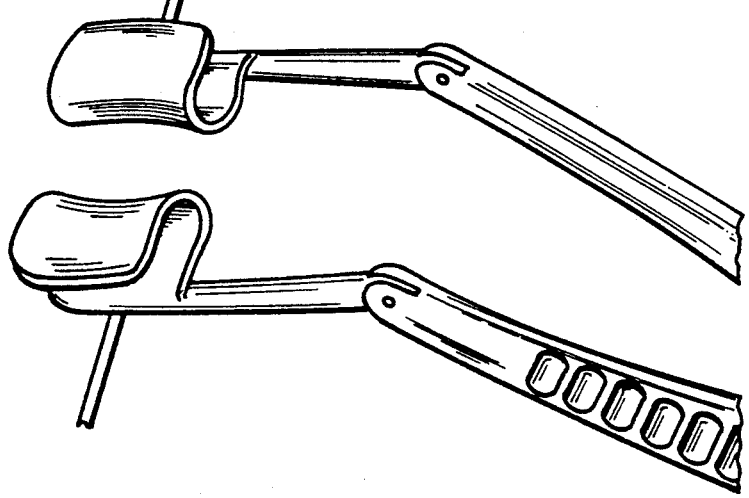

In column 1, line 54, change the words "FIG. 1 is a view" to --FIGS. 1 and 1a are views--.

Figure 3A:
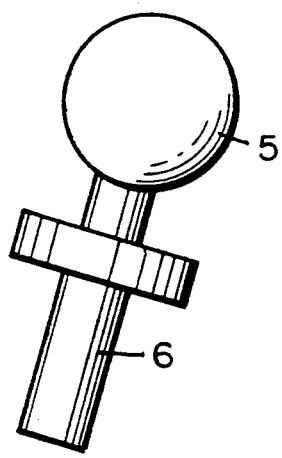
Figure 3B:
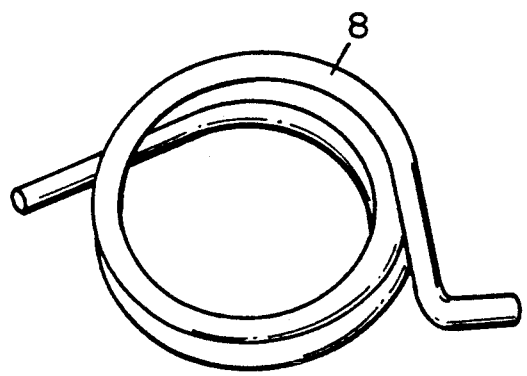

In column 1, line 58, change the words "FIG. 3 is a detail view" to --FIGS. 3, 3a and 3b are detail views--.

In column 1, line 63, between the numeral "5," and the word "the" insert the word --and--.

In column 4, line 47, change the word "tissue" to --tissues--.

Signed and Sealed this

Ninth Day of March, 1993

*Attest:*

STEPHEN G. KUNIN

*Attesting Officer*    Acting Commissioner of Patents and Trademarks

UNITED STATES PATENT AND TRADEMARK OFFICE
CERTIFICATE OF CORRECTION

PATENT NO. : 5,070,860

DATED : December 10, 1991

INVENTOR(S) : Pierre-Alain Grounauer

It is certified that error appears in the above-identified patent and that said Letters Patent is hereby corrected as shown below:

Title page:

Item (30): delete "2/1981 Denmark" and insert in lieu thereof --7/1981 Germany--.

In line 2 of "Foreign Patent Documents" on the title page of the Patent as issued, please delete "Denmark" and insert in lieu thereof --Germany--.

Signed and Sealed this

Fifteenth Day of June, 1993

Attest:

MICHAEL K. KIRK

Attesting Officer

Acting Commissioner of Patents and Trademarks